United States Patent
Gibson

(10) Patent No.: US 9,439,781 B2
(45) Date of Patent: Sep. 13, 2016

(54) PATIENT-MATCHED GUIDES FOR ORTHOPEDIC IMPLANTS

(75) Inventor: Luke Andrew Gibson, Greensburg, IN (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 14/115,330

(22) PCT Filed: May 3, 2012
(Under 37 CFR 1.47)

(86) PCT No.: PCT/US2012/036308
§ 371 (c)(1),
(2), (4) Date: Jul. 11, 2014

(87) PCT Pub. No.: WO2012/151393
PCT Pub. Date: Nov. 8, 2012

(65) Prior Publication Data
US 2014/0336660 A1    Nov. 13, 2014

Related U.S. Application Data

(60) Provisional application No. 61/481,873, filed on May 3, 2011.

(51) Int. Cl.
*A61F 2/46* (2006.01)
*A61F 2/30* (2006.01)

(52) U.S. Cl.
CPC .......... *A61F 2/4609* (2013.01); *A61F 2/30942* (2013.01); *A61F 2002/305* (2013.01); *A61F 2002/4687* (2013.01); *Y10T 29/49* (2015.01)

(58) Field of Classification Search
CPC .............. A61B 17/92; A61B 2017/90; A61B 2017/922; A61B 2017/924; A61B 2017/927; A61F 2/46; A61F 2/4603–2/461; A61F 2/4612; A61F 2/4684; A61F 2002/3411
See application file for complete search history.

(56) References Cited

U.S. PATENT DOCUMENTS

| | | |
|---|---|---|
| 3,874,003 A | 4/1975 | Moser et al. |
| 3,882,550 A | 5/1975 | Karpf et al. |
| 3,894,297 A | 7/1975 | Mittelmeier et al. |
| 4,141,088 A | 2/1979 | Treace et al. |
| 4,250,361 A | 2/1981 | Dvorachek |
| 4,437,193 A | 3/1984 | Oh |

(Continued)

OTHER PUBLICATIONS

International Search Report/Written Opinion dated Nov. 20, 2012 for PCT/US2012/036308.

(Continued)

*Primary Examiner* — Matthew Lawson
*Assistant Examiner* — Amy Sipp
(74) *Attorney, Agent, or Firm* — David Chambers, Esq.

(57) ABSTRACT

Systems, devices, and methods are provided for implanting and aligning orthopedic implants. A patient-matched alignment guide is used to orient tools and implants intraoperatively. In certain embodiments, the systems, devices, and methods include an orthopedic guide comprising a body having a bottom surface, wherein at least a portion of the bottom surface has predetermined surface characteristics that correspond to respective characteristics of a patient's bony anatomy, and a pliable flange that extends from the bottom surface and is shaped to be received within an undercut of an implant to releasably couple the orthopedic guide to the implant.

8 Claims, 12 Drawing Sheets

(56) References Cited

U.S. PATENT DOCUMENTS

| | | | |
|---|---|---|---|
| 4,473,068 A | 9/1984 | Oh | |
| 4,475,549 A | 10/1984 | Oh | |
| 4,623,352 A | 11/1986 | Oh | |
| 4,632,111 A * | 12/1986 | Roche | 606/53 |
| 4,673,409 A | 6/1987 | Van Kampen | |
| 4,676,799 A | 6/1987 | Legrand | |
| 4,718,908 A | 1/1988 | Wigginton et al. | |
| 4,795,469 A | 1/1989 | Oh | |
| 4,883,490 A | 11/1989 | Oh | |
| 4,990,149 A | 2/1991 | Fallin | |
| 4,995,883 A | 2/1991 | Demane et al. | |
| 4,997,447 A | 3/1991 | Shelley | |
| 5,047,033 A | 9/1991 | Fallin | |
| 5,078,746 A | 1/1992 | Garner | |
| 5,080,677 A | 1/1992 | Shelley | |
| 5,098,437 A * | 3/1992 | Kashuba et al. | 606/89 |
| 5,108,452 A | 4/1992 | DeMane et al. | |
| 5,171,243 A * | 12/1992 | Kashuba et al. | 606/86 R |
| 5,171,313 A * | 12/1992 | Salyer | 606/86 R |
| 5,193,679 A | 3/1993 | White | |
| 5,217,499 A | 6/1993 | Shelley | |
| 5,226,917 A | 7/1993 | Schryver | |
| 5,284,483 A * | 2/1994 | Johnson et al. | 606/86 R |
| 5,310,408 A | 5/1994 | Schryver et al. | |
| 5,314,487 A | 5/1994 | Schryver et al. | |
| 5,324,291 A | 6/1994 | Ries et al. | |
| 5,350,381 A | 9/1994 | Melton | |
| 5,358,532 A | 10/1994 | Evans et al. | |
| 5,405,005 A | 4/1995 | White | |
| 5,405,392 A | 4/1995 | Deckner | |
| 5,456,717 A | 10/1995 | Zweymuller et al. | |
| 5,507,830 A | 4/1996 | Demane et al. | |
| 5,527,317 A * | 6/1996 | Ashby et al. | 606/91 |
| 5,540,697 A * | 7/1996 | Rehmann et al. | 606/91 |
| 5,549,702 A | 8/1996 | Ries et al. | |
| 5,571,105 A | 11/1996 | Gundolf | |
| 5,584,837 A * | 12/1996 | Petersen | 606/91 |
| 5,593,446 A | 1/1997 | Kuoni | |
| 5,676,704 A | 10/1997 | Ries et al. | |
| 5,782,928 A | 7/1998 | Ries et al. | |
| 5,879,355 A * | 3/1999 | Ullmark | 606/93 |
| 5,879,402 A * | 3/1999 | Lawes et al. | 128/898 |
| 5,879,405 A | 3/1999 | Ries et al. | |
| 5,931,870 A | 8/1999 | Cuckler et al. | |
| 5,976,148 A * | 11/1999 | Charpenet et al. | 606/91 |
| 6,019,766 A * | 2/2000 | Ling et al. | 606/94 |
| 6,059,833 A | 5/2000 | Doets | |
| 6,132,469 A * | 10/2000 | Schroeder | 623/22.24 |
| 6,136,037 A | 10/2000 | Hassig et al. | |
| 6,162,227 A | 12/2000 | Eckhardt et al. | |
| 6,270,502 B1 | 8/2001 | Stulberg | |
| 6,325,829 B1 | 12/2001 | Schmotzer | |
| 6,344,060 B1 | 2/2002 | Schmotzer et al. | |
| 6,383,228 B1 | 5/2002 | Schmotzer | |
| 6,436,147 B1 | 8/2002 | Zweymuller | |
| 6,451,058 B2 | 9/2002 | Tuke et al. | |
| RE38,058 E | 4/2003 | Fallin | |
| 6,540,788 B1 | 4/2003 | Zweymuller | |
| 6,613,094 B2 | 9/2003 | Zweymuller | |
| 6,626,913 B1 | 9/2003 | McKinnon et al. | |
| 6,652,589 B2 | 11/2003 | Schmotzer et al. | |
| 6,746,452 B2 | 6/2004 | Tuke et al. | |
| 6,808,539 B2 | 10/2004 | Zweymuller | |
| 6,916,342 B2 | 7/2005 | Frederick et al. | |
| 6,986,792 B2 | 1/2006 | McLean et al. | |
| 7,004,973 B2 | 2/2006 | Zweymuller | |
| 7,074,241 B2 | 7/2006 | McKinnon | |
| 7,160,307 B2 | 1/2007 | Harwood et al. | |
| 7,160,332 B2 | 1/2007 | Frederick et al. | |
| 7,175,668 B2 | 2/2007 | Zweymuller | |
| 7,179,297 B2 | 2/2007 | McLean | |
| 7,250,054 B2 | 7/2007 | Allen et al. | |
| 7,255,701 B2 | 8/2007 | Allen et al. | |
| 7,335,207 B1 * | 2/2008 | Smith | 606/99 |
| 7,335,231 B2 | 2/2008 | McLean | |
| 7,374,576 B1 | 5/2008 | Ries et al. | |
| 7,455,693 B2 | 11/2008 | Zweymuller | |
| 7,494,510 B2 | 2/2009 | Zweymuller | |
| 7,497,875 B2 | 3/2009 | Zweymuller | |
| 7,534,271 B2 | 5/2009 | Ries et al. | |
| 7,575,603 B2 | 8/2009 | Bergin et al. | |
| 7,591,821 B2 | 9/2009 | Kelman | |
| 7,621,915 B2 | 11/2009 | Frederick et al. | |
| 7,682,398 B2 | 3/2010 | Croxton et al. | |
| 7,749,277 B2 | 7/2010 | McLean | |
| 7,749,278 B2 | 7/2010 | Frederick et al. | |
| 7,780,667 B2 | 8/2010 | Watanabe et al. | |
| 7,828,806 B2 | 11/2010 | Graf et al. | |
| 7,863,410 B2 | 1/2011 | Smith et al. | |
| 7,879,106 B2 | 2/2011 | McMinn | |
| 7,892,290 B2 | 2/2011 | Bergin et al. | |
| 7,901,411 B2 | 3/2011 | Frederick et al. | |
| 2003/0171818 A1 | 9/2003 | Lewallen | |
| 2003/0187512 A1* | 10/2003 | Frederick et al. | 623/22.2 |
| 2005/0148843 A1* | 7/2005 | Roose | 600/407 |
| 2007/0005144 A1* | 1/2007 | Leisinger et al. | 623/22.29 |
| 2007/0173856 A1* | 7/2007 | Parker | 606/99 |
| 2007/0219562 A1* | 9/2007 | Slone et al. | 606/99 |
| 2007/0219640 A1* | 9/2007 | Steinberg | 623/22.12 |
| 2008/0077249 A1* | 3/2008 | Gradel | 623/22.15 |
| 2009/0163922 A1* | 6/2009 | Meridew et al. | 606/88 |
| 2010/0063597 A1* | 3/2010 | Gradel | 623/23.43 |
| 2010/0082035 A1* | 4/2010 | Keefer | 606/91 |
| 2010/0274253 A1 | 10/2010 | Ure | |
| 2010/0318192 A1* | 12/2010 | Laffay et al. | 623/22.21 |
| 2011/0224674 A1* | 9/2011 | White et al. | 606/91 |
| 2012/0041445 A1* | 2/2012 | Roose et al. | 606/96 |
| 2012/0053592 A1* | 3/2012 | Burgi | 606/91 |
| 2012/0303035 A1* | 11/2012 | Geebelen | 606/91 |
| 2013/0158558 A1* | 6/2013 | Preuss et al. | 606/91 |

OTHER PUBLICATIONS

Australian Patent Office, First Examination Report, dated Feb. 15, 2016, 3 pages.

Japanese Patent Office, First Office Action, dated Mar. 14, 2016, 11 pages including translation.

* cited by examiner

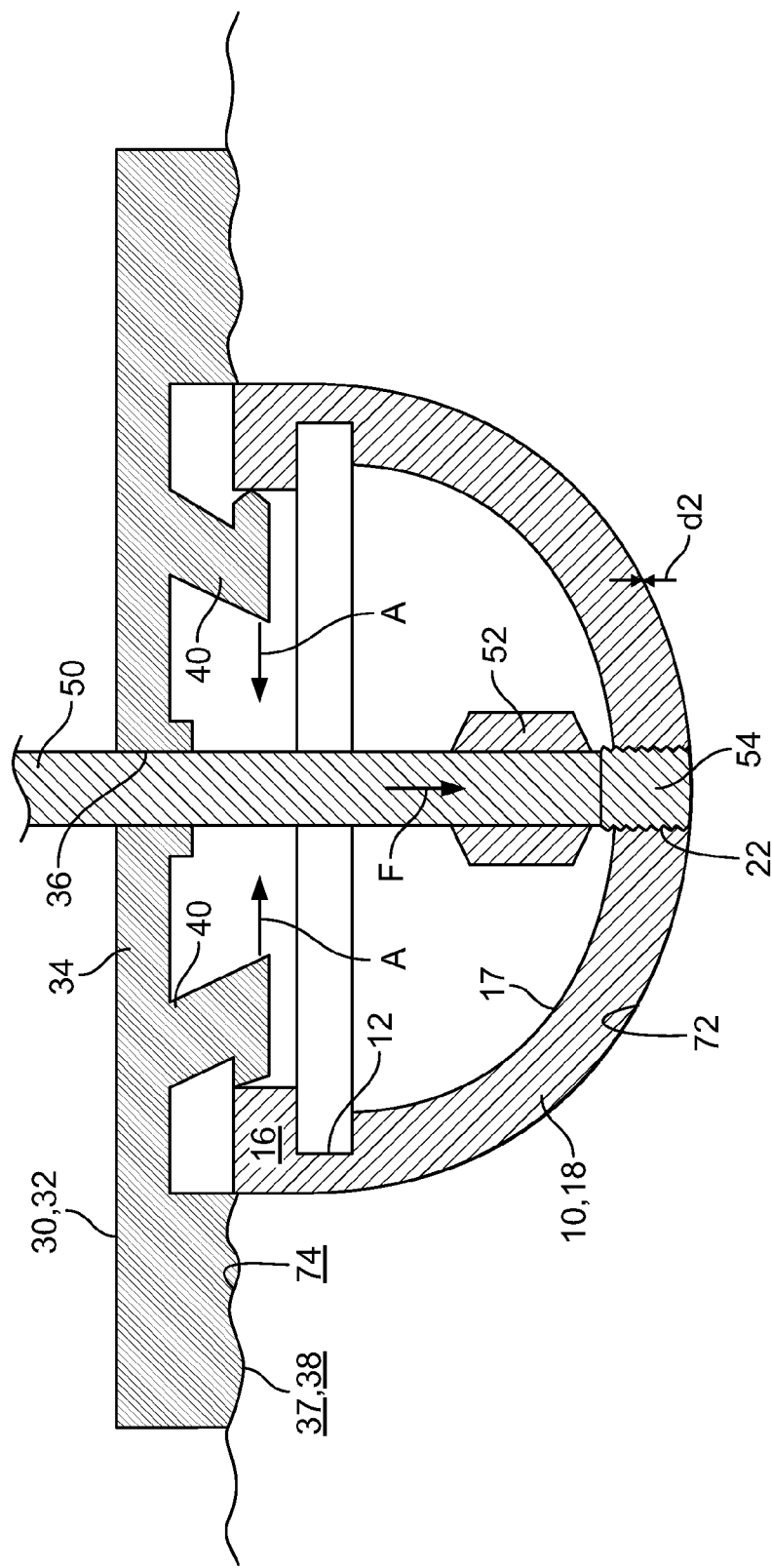

PATIENT-MATCHED GUIDES FOR ORTHOPEDIC IMPLANTS

CROSS-REFERENCE TO RELATED APPLICATIONS

This application claims the benefit of U.S. Provisional Patent Application No. 61/481,873, filed May 3, 2011, which is hereby incorporated by reference herein in its entirety.

BACKGROUND

Surgeons use a variety of surgical instruments when performing a hip arthroplasty to implant a prosthesis such as an acetabular cup into a patient's acetabulum. For example, the surgeon typically uses a reamer or other cutting device to ream the acetabulum to form a socket within which the acetabular cup can be implanted. An impactor may then be used to drive the acetabular cup into place within the acetabulum. When operating, in many instances it will be important for the surgeon to position and orient the surgical instruments as precisely as possible, so that the acetabular cup will ultimately be positioned and oriented as intended. Otherwise, if the acetabular cup is not properly positioned and oriented (for example, if the acetabular cup has too shallow or too high of a cup inclination angle), the patient may experience excessive wear on the acetabular cup, or other components used with the acetabular cup, as well as dislocation, impingement, limited ranges of motion, infection, or rejection of the implant.

SUMMARY

Disclosed herein are systems, devices, and methods for implanting and aligning orthopedic implants. In certain implementations, the systems, devices, and methods include a guide having a surface that is at least in part patient-matched (e.g., to a particular patient's acetabular rim) such that the guide fits in a preferred position and orientation around the perimeter of the acetabular rim. The guide may be used to align and impact an orthopedic implant (e.g., an acetabular cup) into the patient's anatomy.

In certain embodiments, the systems, devices, and methods include an orthopedic guide comprising a body having a bottom surface, wherein at least a portion of the bottom surface has predetermined surface characteristics that correspond to respective characteristics of a patient's bony anatomy, and a pliable flange that extends from the bottom surface and is shaped to be received within an undercut of an implant to releasably couple the orthopedic guide to the implant. In certain embodiments, the guide further comprises an opening in the body. A crossbar may be disposed in the opening, wherein the crossbar comprises an aperture configured to receive an impactor. The aperture has a diameter sized to allow the orthopedic guide to slide along the impactor. In certain embodiments, the predetermined surface characteristics are disposed along the entirety of the bottom surface. In certain embodiments, the predetermined surface characteristics further comprise a texture, wherein the texture is selected from the group consisting of serrations, points, cross-hatches, grooves, ridges, bumps, and barbs. In certain embodiments, the flange includes a first end proximate to the bottom surface and a second end distal to the bottom surface. The flange may be configured to pivot about the first end relative to the bottom surface. In certain embodiments, the second end is tapered along a first edge, or the second end comprises a dual tapered edge. In certain embodiments, the guide includes a plurality of flanges.

In certain embodiments, an orthopedic implant assembly is provided and comprises an implant and an orthopedic guide. The orthopedic guide may include an opening, wherein the opening is shaped to correspond to a diameter of the implant. In certain embodiments, the implant comprises a central aperture, wherein the opening and the central aperture are collinear. The guide body may have a diameter greater than a diameter of the implant.

In certain embodiments, methods for aligning an orthopedic implant include coupling a guide to the orthopedic implant using a snap-fit flange, wherein the guide has a predetermined configuration that corresponds to a respective anatomic landmark site, aligning the orthopedic implant using the guide, and removing the guide from the orthopedic implant by actuating the snap-fit flange. In certain embodiments, the aligning further comprises placing the guide in the predetermined configuration by matching the guide with the respective anatomic landmark site. The method may further include determining the fit of the orthopedic implant by viewing the orthopedic implant through an opening in the guide. The guide may be coupled to an impactor, and the orthopedic implant may be coupled to the impactor. In certain embodiments, an attachment piece may be placed onto the impactor at a position between the guide and the orthopedic implant. A force may be applied using the impactor, and the force may simultaneously set the implant in a preferred orientation and actuate the snap-fit flange to decouple the guide from the implant. In certain embodiments, the implant is free to rotate when the guide makes contact with a patient's anatomy.

In certain embodiments, a kit is provided that includes at least one guide comprising a body having a bottom surface, wherein at least a portion of the bottom surface has predetermined surface characteristics that correspond to respective characteristics of a patient's bony anatomy, and a pliable flange extending from the bottom surface and shaped to be received within an undercut of an implant to releasably couple the orthopedic guide to the implant. The kit may also include an implant configured to couple with the at least one guide. In certain embodiments, the kit includes an impactor.

In certain embodiments, a method for manufacturing an orthopedic alignment guide includes receiving data associated with at least one of an X-ray, a CT scan, and an MRI scan, determining an implant axis based on the received data, determining a respective configuration for the orthopedic guide based on the determined implant axis and the received data, and producing the orthopedic guide according to the determined configuration, where the orthopedic guide includes at least one pliable flange.

In certain embodiments, an orthopedic guide is provided that includes means for aligning the guide relative to a patient's bony anatomy, said means comprising a bottom surface having predetermined surface characteristics that correspond to respective characteristics of the bony anatomy, and means for releasably coupling the orthopedic guide to an implant, said means extending from the bottom surface. In certain embodiments, said means for aligning further comprises an opening. A crossbar may be disposed in the opening, wherein the crossbar comprises an aperture configured to receive an impactor. The aperture has a diameter sized to allow the orthopedic guide to slide along the impactor. In certain embodiments, the predetermined surface characteristics are disposed along the entirety of the bottom surface. In certain embodiments, the predetermined surface characteristics further comprise a texture, wherein the texture is selected from the group consisting of serrations, points, cross-hatches, grooves, ridges, bumps, and barbs. In certain embodiments, said means for releasably coupling comprises a first end proximate to the bottom surface and a second end distal to the bottom surface. The means for releasably coupling may be configured to pivot about the first end relative to the bottom surface. In certain embodiments, the second end is tapered along a first edge, or the second end comprises a dual tapered edge. In certain embodiments, a plurality of means for releasably coupling the orthopedic guide to an implant may be provided.

Variations and modifications of these embodiments will occur to those of skill in the art after reviewing this disclosure. The foregoing features and aspects may be implemented, in any combination and subcombination (including multiple dependent combinations and subcombinations), with one or more other features described herein. The various features described or illustrated herein, including any components thereof, may be combined or integrated in other systems. Moreover, certain features may be omitted or not implemented.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which:

FIGS. 8A-8C show various schematic cross-sectional views of FIG. 7B taken along the line 8-8;

DETAILED DESCRIPTION

To provide an overall understanding of the systems, devices, and methods described herein, certain illustrative embodiments will be described. Although the embodiments and features described herein are specifically described for use in connection with acetabular systems, it will be understood that all the components, connection mechanisms, adjustable systems, manufacturing methods, and other features outlined below may be combined with one another in any suitable manner and may be adapted and applied to medical devices and implants to be used in other surgical procedures, including, but not limited to knee arthroplasty, spine arthroplasty, cranio-maxillofacial surgical procedures, shoulder arthroplasty, as well as foot, ankle, hand, and other extremity procedures. For example, it will be understood that the devices may be used in procedures on other portions of the anatomy, such as a femoral head, glenoid, humerus, radius, ulna, fibula, tibia, proximal femur, foot, ankle, wrist, extremity, or other bony or cartilaginous regions or other portions of a patient's anatomy.

Figure 1:
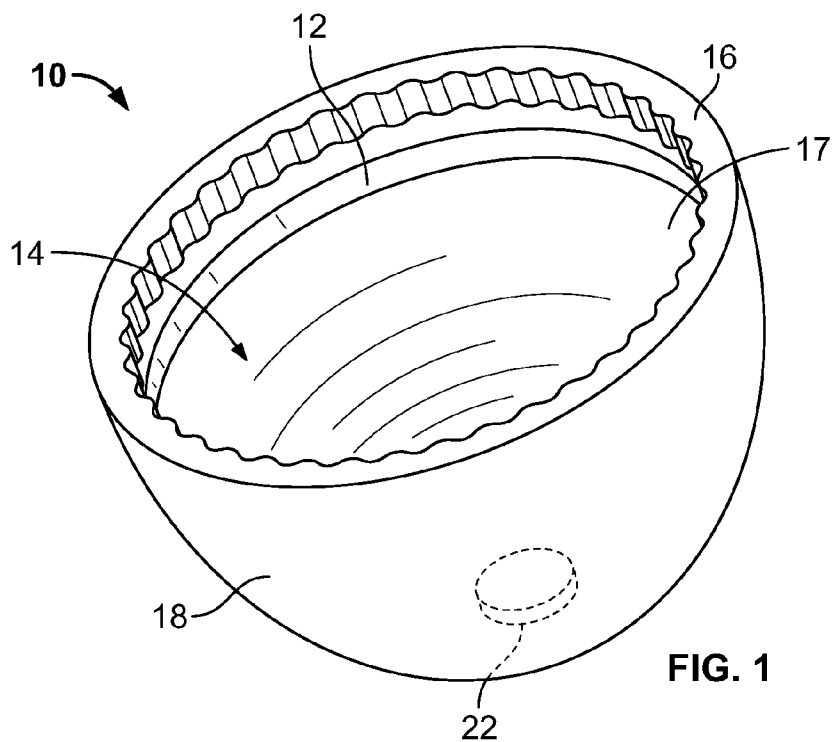
FIG. 1 shows a perspective view of an illustrative implant.

FIG. 1 shows a perspective view of an implant 10 (e.g., an acetabular shell, cup, cage, or augment). The implant 10 includes an implant body 18 that is inserted within a patient's acetabulum 72. As shown in FIG. 1, the implant body 18 has an aperture 22 that may receive a portion of an impactor (e.g., impactor 50 of FIG. 4A) or other suitable alignment tool. The implant 10 further includes an edge 16 about the implant opening 14 and an undercut or groove 12 proximate to the edge 16 and disposed on an inner surface 17 of the implant 10. The geometry and other properties of the implant 10 are non-limiting.

Figure 2A:
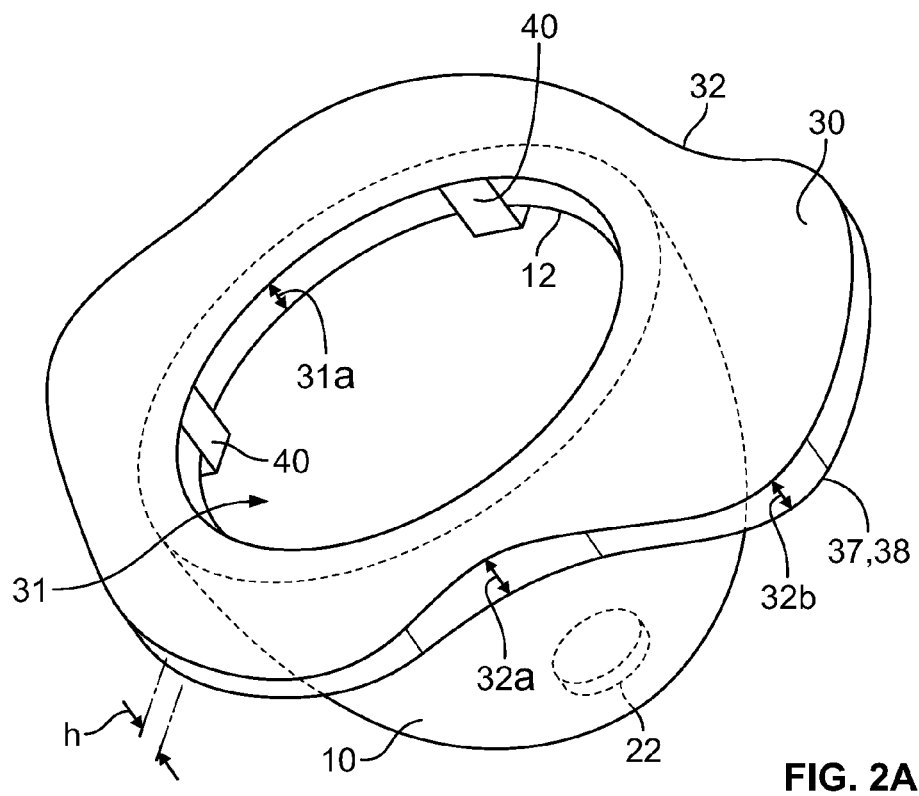
FIGS. 2A and 2B show a perspective view and a schematic cross-sectional view, respectively, of an illustrative guide coupled to the implant of FIG. 1.
Figure 2B:
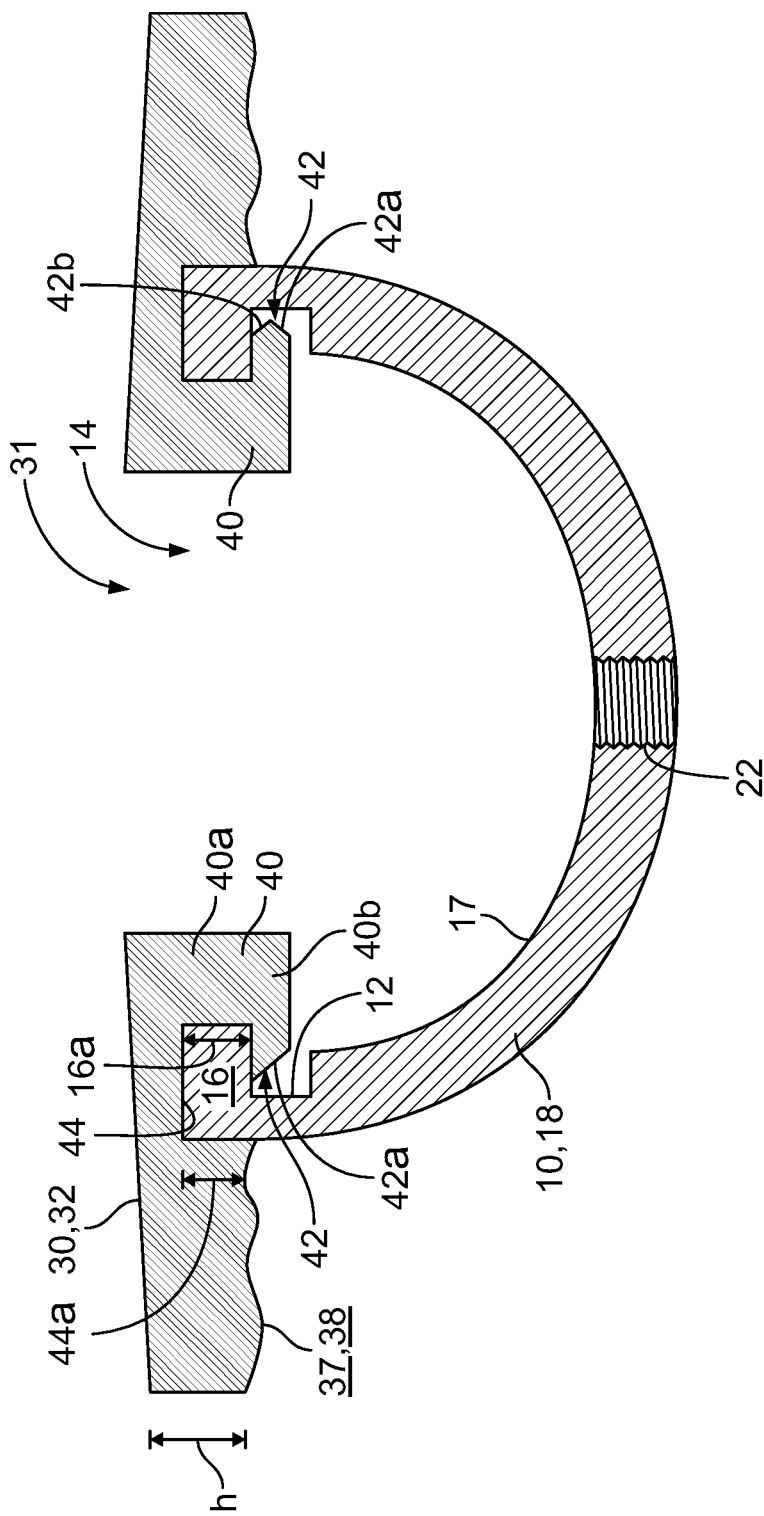

FIGS. 2A and 2B show a perspective view and a schematic cross-sectional view, respectively, of a guide 30 that may be coupled to the implant 10. The guide 30 includes a guide body 32 having an opening 31 that aligns with the implant opening 14. The guide body 32 also has a bottom surface 37 that contacts, at least in part, the patient's acetabular rim 74 and/or bony or other anatomy (e.g., tissue) surrounding the rim 74 (collectively referred to as the acetabular rim 74). At least a portion of the bottom surface 37 of the guide body 32 has a patient-matched surface 38 that substantially conforms to at least a respective portion of the patient's acetabular rim 74. Specifically, the patient-matched surface 38 may have predetermined surface characteristics that correspond to respective characteristics of a patient's bony anatomy. The patient-matched surface 38 may conform or otherwise fit to the acetabular rim 74 in a particular position or orientation. For example, the patient-matched surface 38 may be configured to fit in one position and/or orientation only (e.g., only in the "12 o'clock position" within the acetabulum 72) rather than in multiple positions and/or orientations (e.g., each of the "2 o'clock position" and "4 o'clock position," etc.). In some embodiments, the patient-matched surface 38 extends continuously over the entire bottom surface 37 of the guide 30. In other embodiments, it does not; rather, only select portions of the bottom surface 37 comprise the patient-matched surface 38. These select portions may be determined, for example, by a surgeon prior to the operation or may be automatically determined using appropriate computational resources such as those discussed below with reference to FIGS. 9 and 10. In some embodiments, the entirety of the bottom surface 37 that contacts the patient's acetabular rim 74 is patient-matched. If desired, the patient-matched surface 38 may be textured to improve the overall stability of the guide 30 with respect to the patient's acetabular rim 74. For example, the texturing may include serrations, points, cross-hatches, grooves, ridges, bumps, barbs, any other suitable feature that increases the friction between the patient's acetabular rim 74 and the patient-matched surface 38, or any combination thereof.

The guide body 32 has a generally elliptical shape that is oversized relative to the patient's acetabulum 72 so that the bottom surface 37 of the guide 30 may contact, at least in part, the acetabular rim 74. The guide body 32 may be asymmetrical or symmetrical relative to the acetabulum 72. The guide body 32 may also have a thickness with height, h. In some embodiments the height varies along the guide body 32 at various cross-sections. For example, as shown in FIG. 2A, the guide body 32 includes edge thicknesses 32a and 32b, which may be determined based on the patient-matched data used to manufacture the guide 30. The oversized dimensions of the guide body 32 relative to the patient's acetabulum 72 also allow the guide 30 to mate with and overlay the implant 10. When the guide 30 is overlaid over an implant such as implant 10, a surgeon may be able to view or otherwise visually inspect the implant through the opening 31 provided in the guide body 32. The opening 31 is substantially parallel with the implant opening 14 and thereby aligned with the implant. The edge 16 of the implant 10 is received within a slot 44 (FIG. 2B) formed in the bottom surface 37 of the guide 30. The slot 44 has a height 44a that complements that height 16a of the implant 10 from the edge 16 to the undercut 12, although in certain embodiments the slot 44 may have a height 44a that is relatively greater than height 16a. The implant 10 is coupled to the guide 30 via the flange 40.

As shown in FIGS. 2A and 2B, the guide 30 includes a flange 40 having an end 42 that is received within the undercut 12 of the implant 10. Any suitable number of flanges (e.g., one or more) may be provided. For example, a single flange may extend about substantially the entire opening 31 of the guide body 32, or any suitable portion thereof. In some embodiments, two or more flanges may be spaced apart symmetrically, or asymmetrically, about the opening 31. The flange 40 extends from the bottom surface 37 of the guide 30 and is shaped to be received within the undercut 12 of the implant 10 to releasably couple the guide 30 to the implant 10. The flange 40 includes a first end 40a proximate the bottom surface 37 and a second end 40b distal to the bottom surface 37. In some embodiments, the flange 40 pivots or otherwise flexes about the first end 40a relative to the bottom surface 37. The second end 40b of the flange 40 includes a tip 42 that is tapered on one or both edges 42a and 42b, which taper can affect or be designed to adjust the force needed to couple the flange 40 with the undercut recess 12 of the implant 10. In use, a surgeon "snaps" the flange 40 of the guide 30 into the undercut 12 of the implant 10, and the edge 16 of the implant is received within the slot 44 in the bottom surface 37 of the guide 30. In particular, the flange 40 may be pliable such that it can flex or otherwise deflect against the inner surface 17 of the implant 10 until it is received within the undercut 12.

Figure 3:
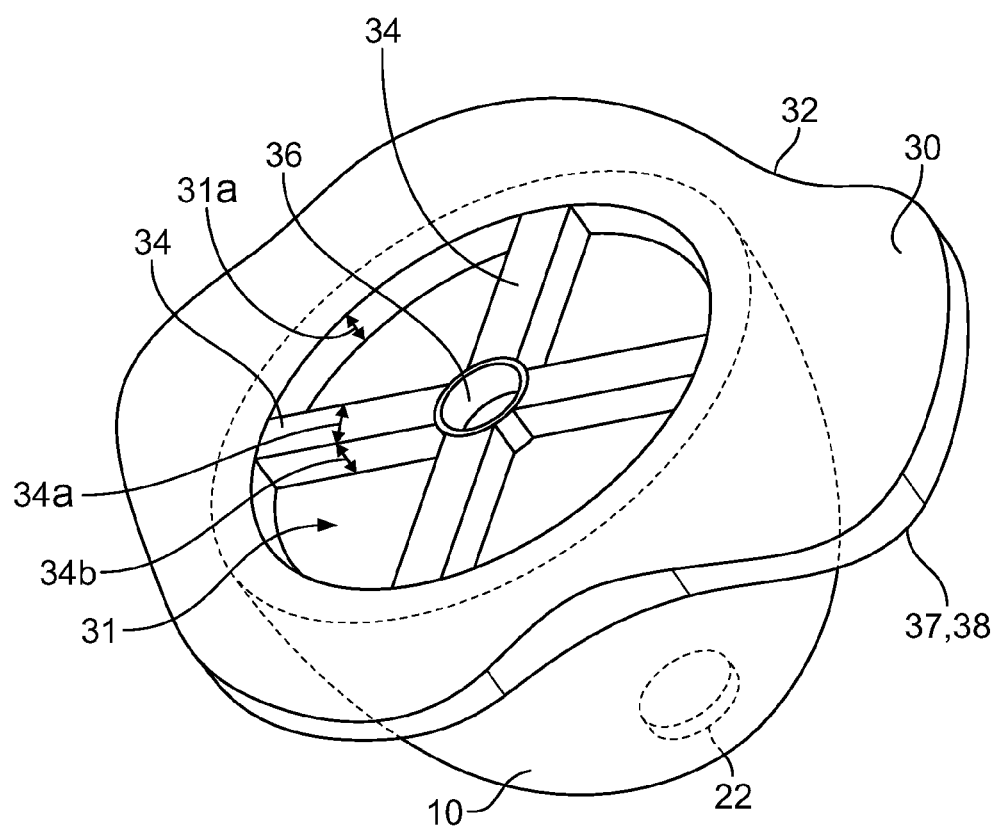
FIG. 3 shows a perspective view of the guide of FIG. 2A having a crossbar and central aperture.

The guide 30 may be configured with appropriate structure that allows it to be used to align and impact the implant 10 into a patient's acetabulum 72. As an example shown in FIG. 3, the guide 30 is provided with structure, such as crossbars 34 and a central aperture 36, to receive an impactor (e.g., impactor 50 of FIG. 4A) to align and impact the implant 10. In embodiments where the guide 30 does not include a crossbar (e.g., as shown in FIGS. 2A and 2B), the impactor is received through the opening 31 in the guide body 32. As shown in FIG. 3, the crossbars 34 are positioned within the opening 31 of the guide 30 and are oriented substantially parallel with the guide body 32. The crossbars 34 may have any suitable width 34a and height 34b. For example, in some embodiments, the height 34b is greater than, equal to, or less than the height 31a of the opening 31. The structural support (e.g., stability) provided by the crossbars 34 for the impactor may depend on the particular geometry of the crossbars. Although two crossbars 34 having a central aperture 36 are depicted in FIG. 3, it will be understood that any suitable number of crossbars may be provided. The crossbars 34 preferably leave the opening 31 of the guide 30 at least partially unobstructed, thereby allowing a surgeon to intraoperatively view the inner surface 17 of the implant 10 to which the guide 30 is coupled.

Figure 4A:
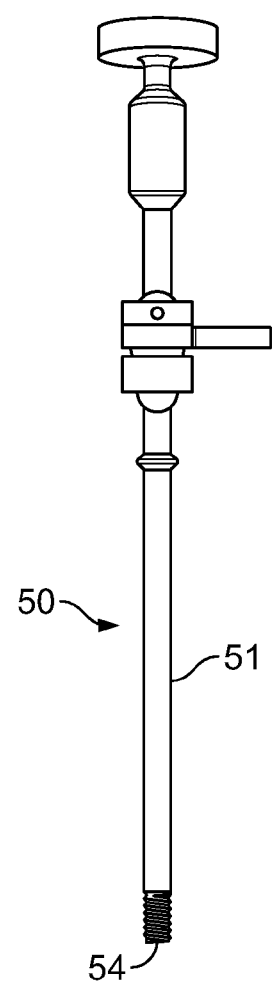
FIGS. 4A and 4B show an illustrative impactor and an optional attachment, respectively, which attachment may be coupled to the impactor.
Figure 4B:
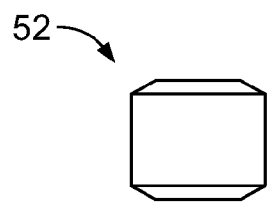

The impactor 50 shown in FIG. 4A may be provided with an optional attachment 52, which is shown in FIG. 4B. In some embodiments, the attachment 52 may help to prevent scratching of the inner surface 17 of the implant 10, which is typically highly polished to reduce friction with a femoral head. In some embodiments, the attachment 52 may reduce the likelihood that the impactor 50 will jam or otherwise bind to the implant 10 during the procedure (e.g., during alignment or impaction). In some embodiments, the attachment 52 is used to further distribute forces transmitted through the implant 10/impactor 50 connection during the impaction process. The attachment 52 may be secured relative to the impactor 50, the implant 10, or both, in any desired manner, including, but not limited to, threading and/or shoulders on one or both of the impactor shaft 51 and the implant 10, any other suitable coupling mechanism, or any combination thereof. It will be understood that the attachment 52 is merely optional and is not necessary.

Figure 5:
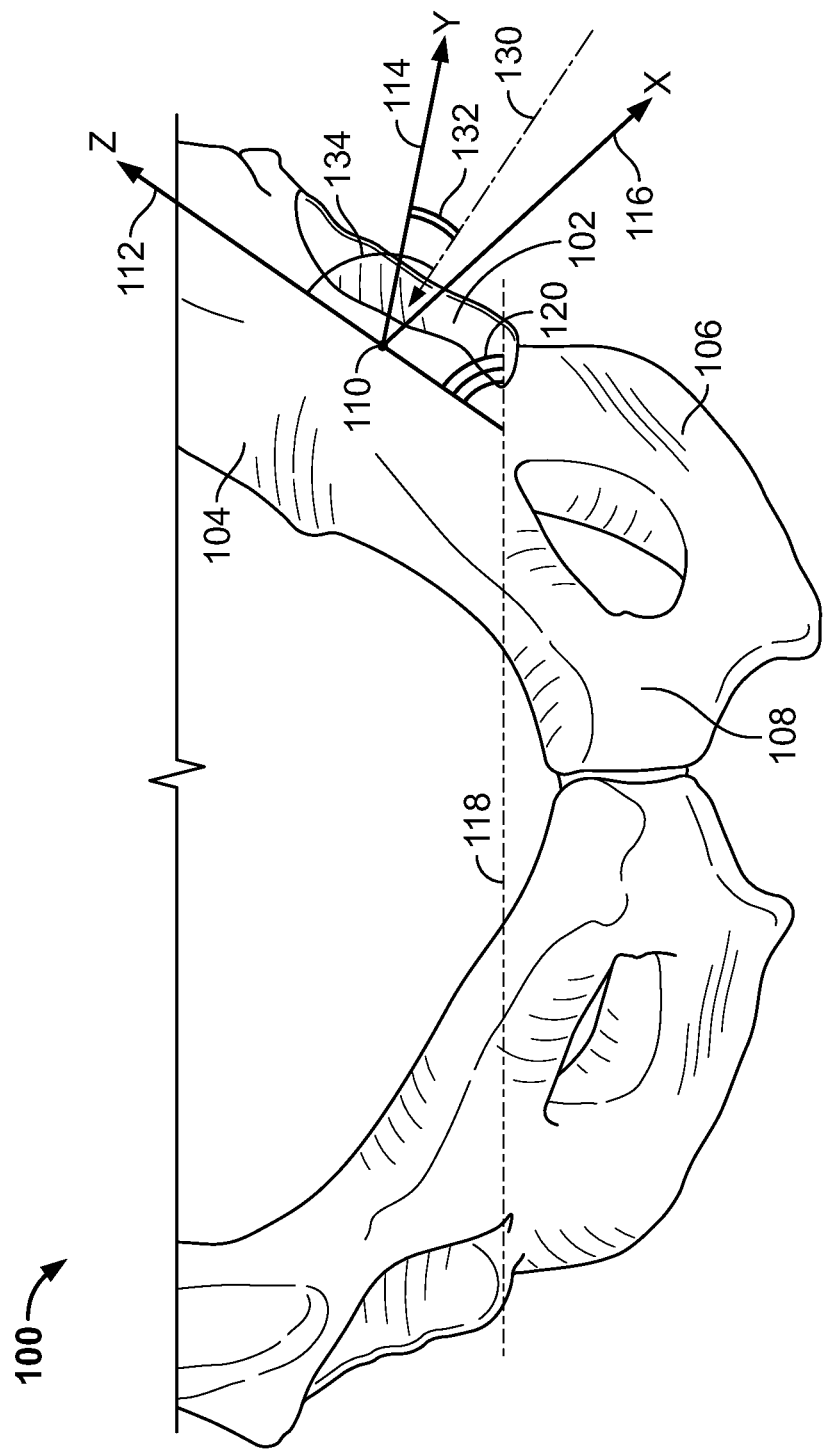
FIG. 5 shows an illustrative pelvic girdle and reference coordinate system.

FIG. 5 shows a pelvic girdle and reference coordinate system that may be used for patient-matched alignment techniques. A patient's pelvic girdle 100 includes acetabulum 102, ilium 104, ischium 106, and pubis 108. A coordinate system, such as a local Cartesian coordinate system, may be used to describe each particular patient's anatomy. For example, the local coordinate system may include origin 110 (e.g., the center of the patient's acetabulum), z-axis 112 (e.g., an axis that extends parallel to the acetabular rim), y-axis 114 (e.g., an axis perpendicular to z-axis 112 in the coronal plane), and x-axis 116 (e.g., an axis orthogonal to y-axis 114 and z-axis 112). Hilgenreiner's line 118 is defined by a horizontal line between the two triradiate cartilage centers of the hips and may be used to determine acetabular angle 120, the angle between Hilgenreiner's line 118 and z-axis 112. As an example, the normal adult range of acetabular angle 120 is approximately between 33 degrees and 38 degrees.

The longitudinal axis of an orthopedic implant tool (e.g., the inserter shaft 51 of a positioner/impactor 50 or other acetabular alignment tool that may or may not have patient-matched features) is aligned with the patient's anatomy to restore the normal center of hip rotation. A desired longitudinal axis for an orthopedic implant tool is denoted by implant axis 130, which may be a patient-matched implant axis indicative of a pre-selected path over which an implant is to be oriented with respect to a patient's bone. Implant axis 130 forms version angle 132 (the angle between y-axis 114 and implant axis 130) and inclination angle 134 (the angle between z-axis 112 and implant axis 130). For example, implant axis 130 may be aligned such that version angle 132 corresponds to 20 degrees of anteversion and inclination angle 134 corresponds to 20 degrees of anteversion.

Figure 6:
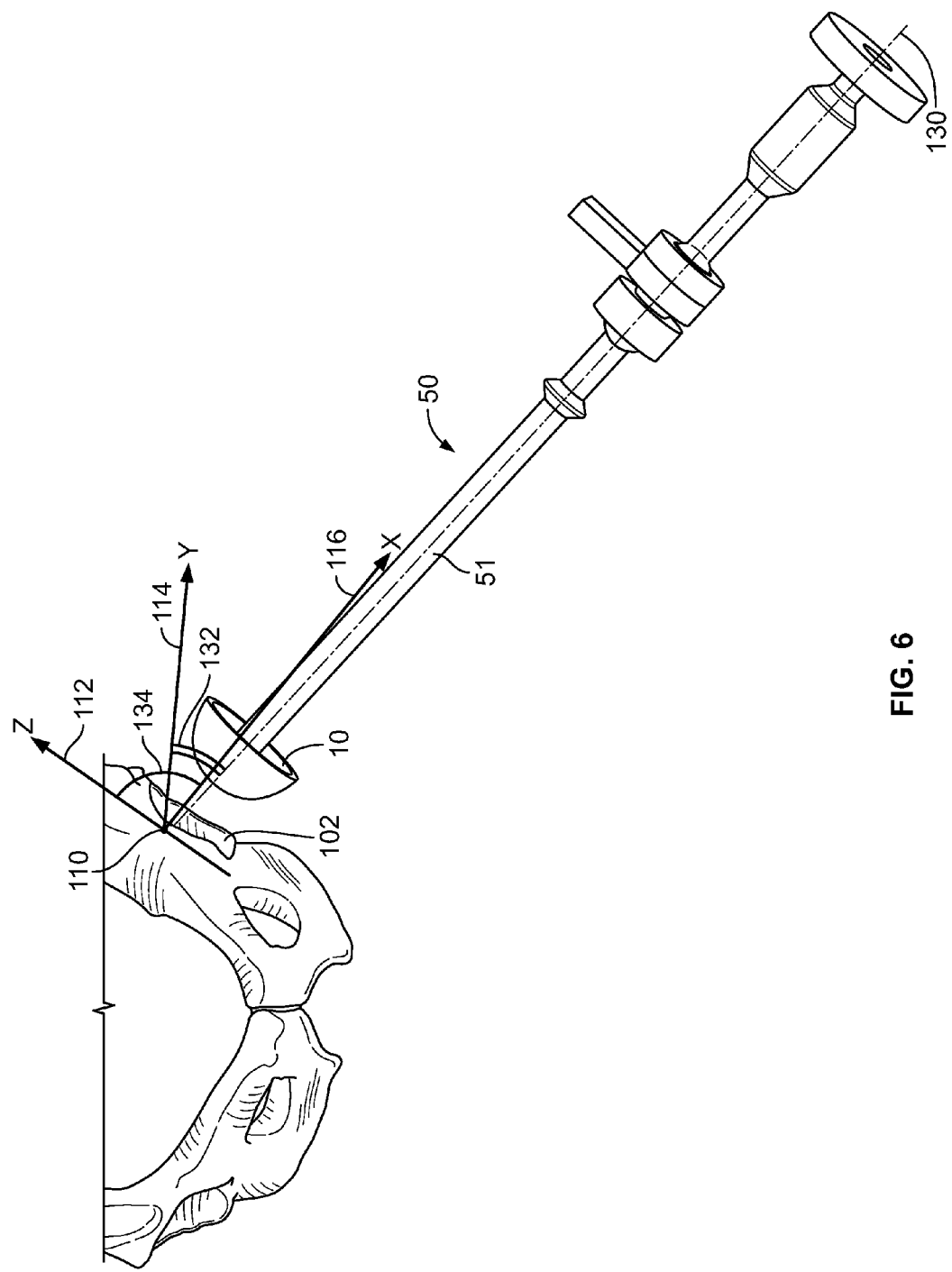
FIG. 6 shows an illustrative acetabular implant system that does not include a guide.

FIG. 6 shows a perspective view of an acetabular implant system that includes acetabulum 102 and positioner/impactor 50. The local coordinate system used to describe the patient's anatomy includes origin 110, z-axis 112, y-axis 114, and x-axis 116. The longitudinal axis of the positioner/impactor 50 is denoted by implant axis 130, which forms version angle 132 and inclination angle 134. The positioner/impactor 50 is coupled to the implant 10 (e.g., an acetabular shell, cup, cage, or augment) at a distal end 54 of the shaft 51 The implant 10 is attached to positioner/impactor 50, inserted into acetabulum 102, seated in acetabulum 102 (e.g., by striking the positioned/impactor 50 with a mallet), and detached from the positioner/impactor 50, which is then removed from the patient's body. As shown in FIG. 6, the system does not include a guide (e.g., guide 30 of FIGS. 2A and 3). Aligning the placement of the implant 10 along implant axis 130 without a guide can be difficult at least because the positioner/impactor 50 can be positioned at any number of positions and orientations. Surgeons typically align an acetabular cup to the patient's acetabulum using an external X-bar located above the operating table on which the patient is positioned. The X-bar is positioned so that the vertical bar of the X-bar is perpendicular to the long axis of the patient's body and the appropriate crossbar (e.g., left or right) aligns with the long axis of the patient's body. However, the use of a generalized X-bar positioning system is often insufficient to properly align the acetabular implant as a result of anatomical differences between patients or differences in patient position during surgery.

Figure 7A:
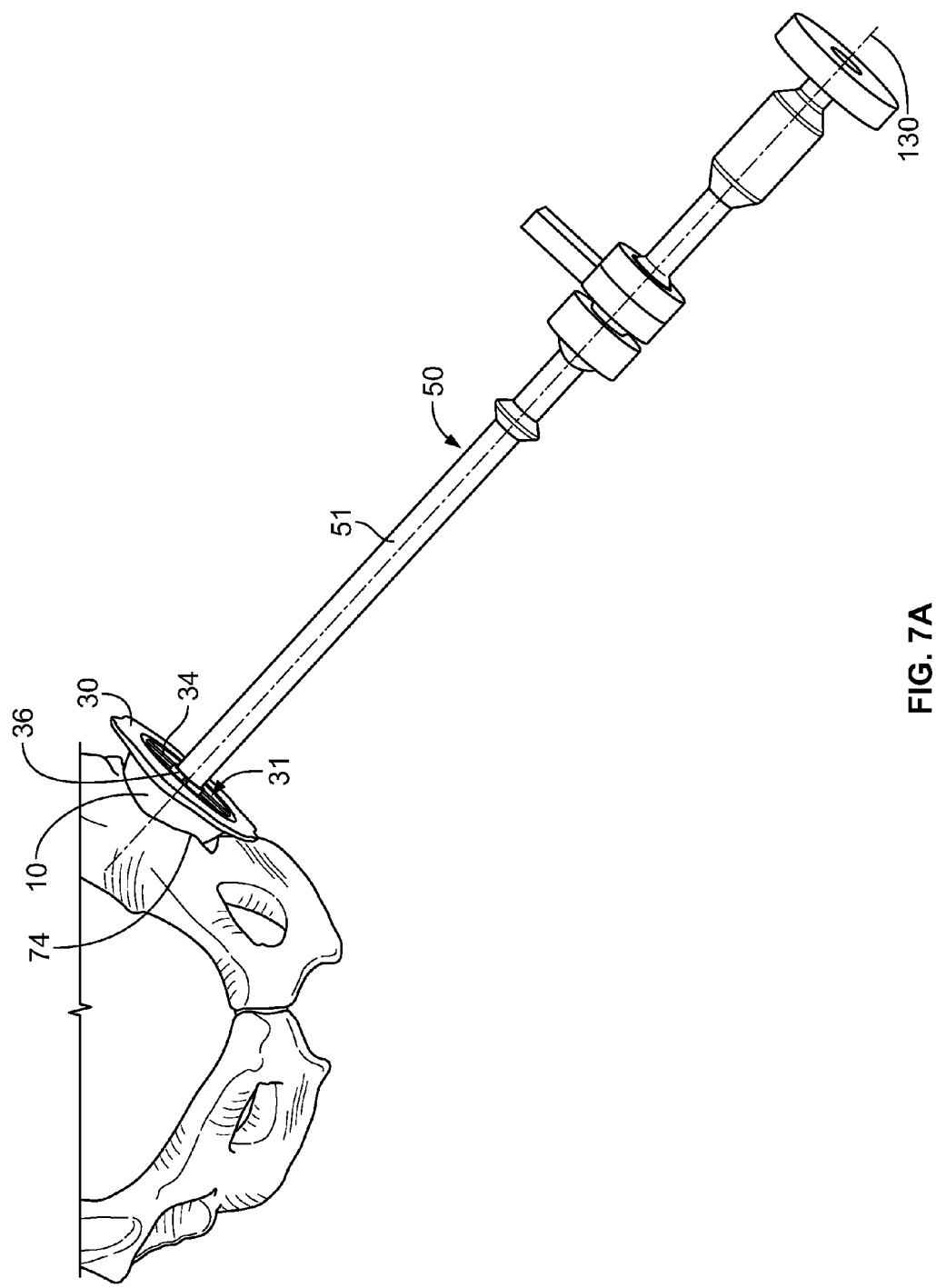
FIGS. 7A and 7B show perspective views of an illustrative patient-matched assembly that includes the guide and implant assembly of FIG. 3 inserted within a patient's acetabulum, with the impactor of FIG. 4A coupled to the assembly.
Figure 7B:
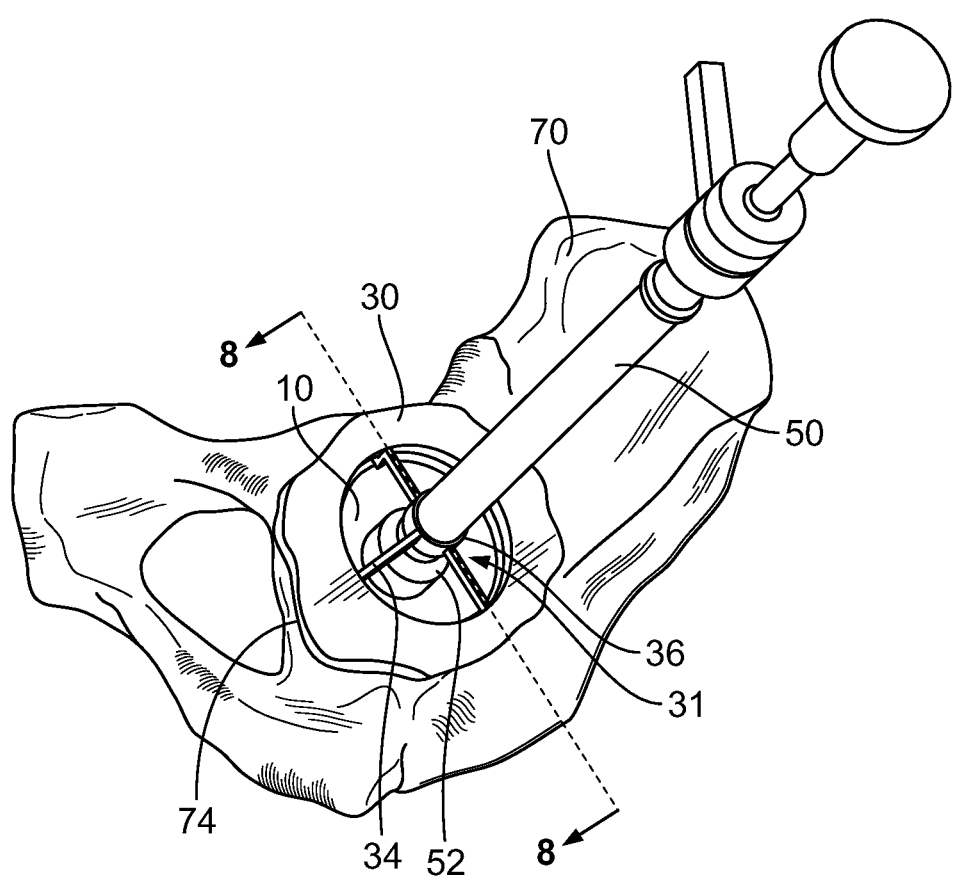
Figure 8A:
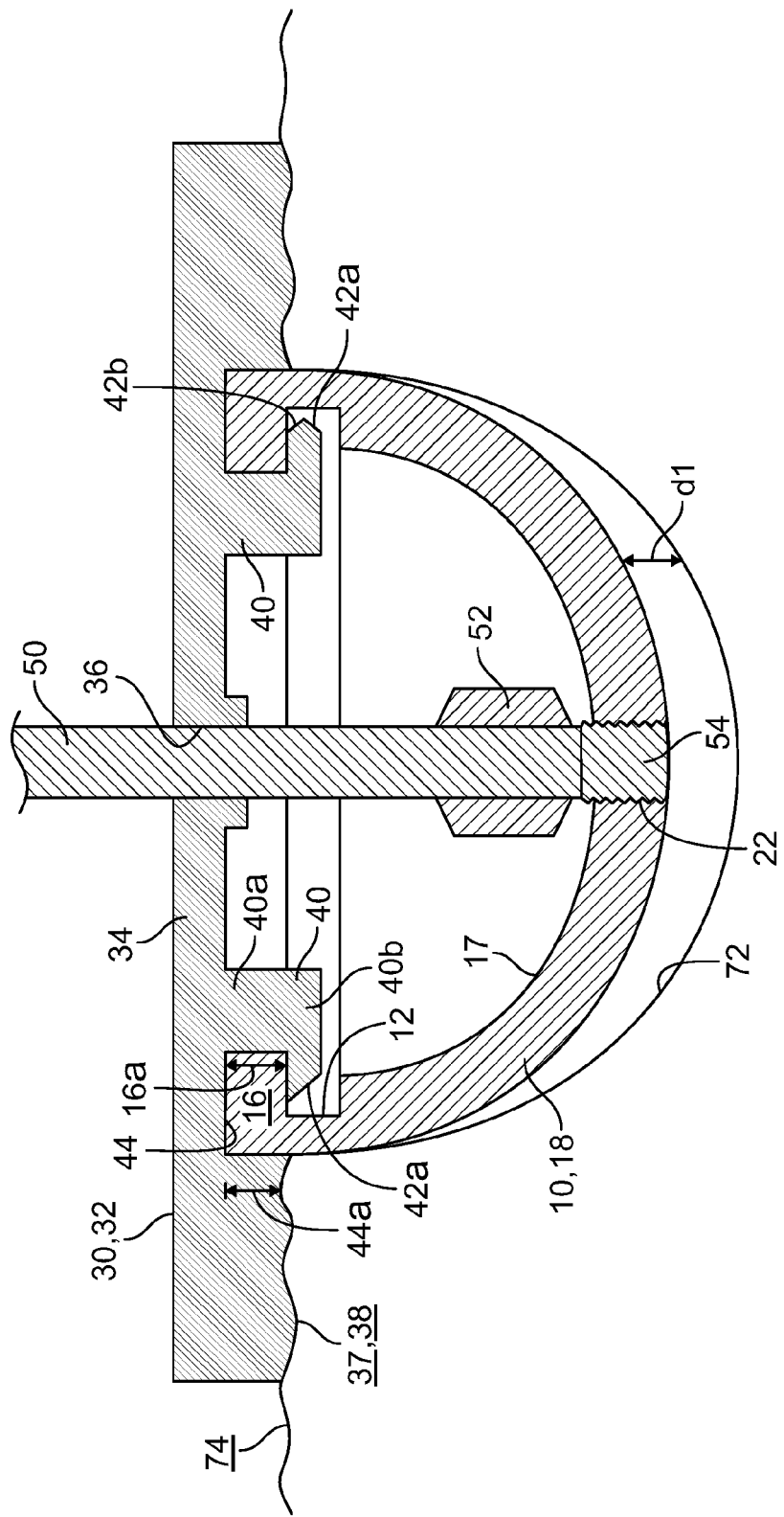

FIGS. 7A and 7B show perspective views of an illustrative patient-matched assembly. To assemble the implant 10, guide 30, and impactor 50 for use during the surgical procedure, a surgeon may first insert the distal end 54 of the impactor 50 through the opening 31 of the guide 30 or through the central aperture 36 of the guide 30, or both. The aperture 36 and the opening 31 have a clearance that allows the guide 30 to slide along the shaft 51 of the impactor 50. For example, the aperture 36 and the opening 31 may have a diameter sized to allow the guide to slide along the impactor 50. Next, if it is desired to use the attachment 52, the attachment 52 may be positioned on the end 54 of the impactor 50. The end 54 of the impactor 50 may be threaded into the aperture 22 of the implant 10 to couple the impactor 50 to the implant 10. After coupling the implant 10 to the end 54 of the impactor 50, the guide 30 (which is free to slide along the impactor 50) is coupled to the implant 10. Specifically, as shown in FIG. 8A, the guide 30 includes a flange 40 that is received within the undercut 12 of the implant 10. A surgeon may "snap" the flange 40 of the guide 30 into the undercut 12 of the implant 10. In particular, the flange 40 may be pliable such that it can flex or otherwise deflect against the inner surface 17 of the implant 10 until it is received within the undercut 12. The flange 40 extends from the bottom surface 37 of the guide 30 and is configured to be received within the undercut 12 of the implant 10 to releasably couple the guide 30 to the implant.

The patient-matched portions 38 of the guide 30 align the implant 10 to particular patient acetabular bony landmarks (e.g., acetabular bony landmarks such as an anterior inferior iliac spine, acetabular limbus, ischial spine, pubic tubercle, acetabular notch, etc.) to align the implant 10 with the implant axis 130. The configuration of the guide 30 is patient-matched by specifically structuring the patient-matched portions with a configuration that, when applied to a particular patient, matches the anatomy of that patient. In particular, the guide 30 has pre-selected or predetermined patient-matched characteristics on patient-matched portion 38, such as shape, length, width, and thickness, so that the guide 30 will be positioned against the patient's bone at specific landmarks in the predetermined configuration. In certain embodiments, the guide 30 is labeled with the anatomic bony landmarks (e.g., acetabular bony landmarks such as an anterior inferior iliac spine, acetabular limbus, ischial spine, pubic tubercle, acetabular notch, etc.) with which the guide 30 should mate or includes other visual indicia (e.g., directional arrows) reflecting the preferred orientation of the guide 30.

In use, the implant 10 may be inserted into the acetabulum 72 as shown in FIGS. 7A-7B and 8A-8C. The edge 16 of the implant 10 is received within a slot 44 formed in the bottom surface 37 of the guide 30. The slot 44 has a height 44a that complements that height 16a of the implant 10 from the edge 16 to the undercut 12, although in certain embodiments the slot 44 may have a height 44a that is relatively greater than height 16a. The implant 10 is coupled to the guide 30 via the flange 40. In the embodiment of FIG. 8A, the guide 30 is dimensioned such that the patient-matched surface 38 of the guide 30 makes contact with the acetabular rim 74 before the body 18 of the implant 10 makes contact with the acetabulum 72, leaving a space, $d_1$, between the implant 10 and the acetabulum 72. In this way, the patient-matched surface 38 may properly align the implant 10 in the desired position and orientation within the acetabulum 72 before impaction. The space, $d_1$, between the implant 10 and the acetabulum 72 prevents, for example, interference between the implant 10 and the patient's acetabulum 72 while the implant 10 is being positioned using the guide 30 (e.g., the implant body 18 does not rub against the acetabulum 72). As shown in FIG. 8A, the edge 16 of the implant 10 is seated above the acetabular rim 74. When the implant 10 is properly aligned, the surgeon applies a force to the impactor 50, which may be translated to the implant 10 through the threaded connection between the impactor 50 and implant 10 (at aperture 22 and end 54) and/or through the coupling between the guide 30 and implant 10 (at flange 40 and undercut 12). The force impacts the implant 10 at the desired position and orientation within the acetabulum 72. Thus, as shown in FIG. 8B, the body 18 of the implant 10 is contacting the acetabulum 72 after having been impacted. Because the implant 10 is contacting the acetabulum 72 there is no or substantially no space, $d_2$, between the implant 10 and the acetabulum 72.

Figure 8C:
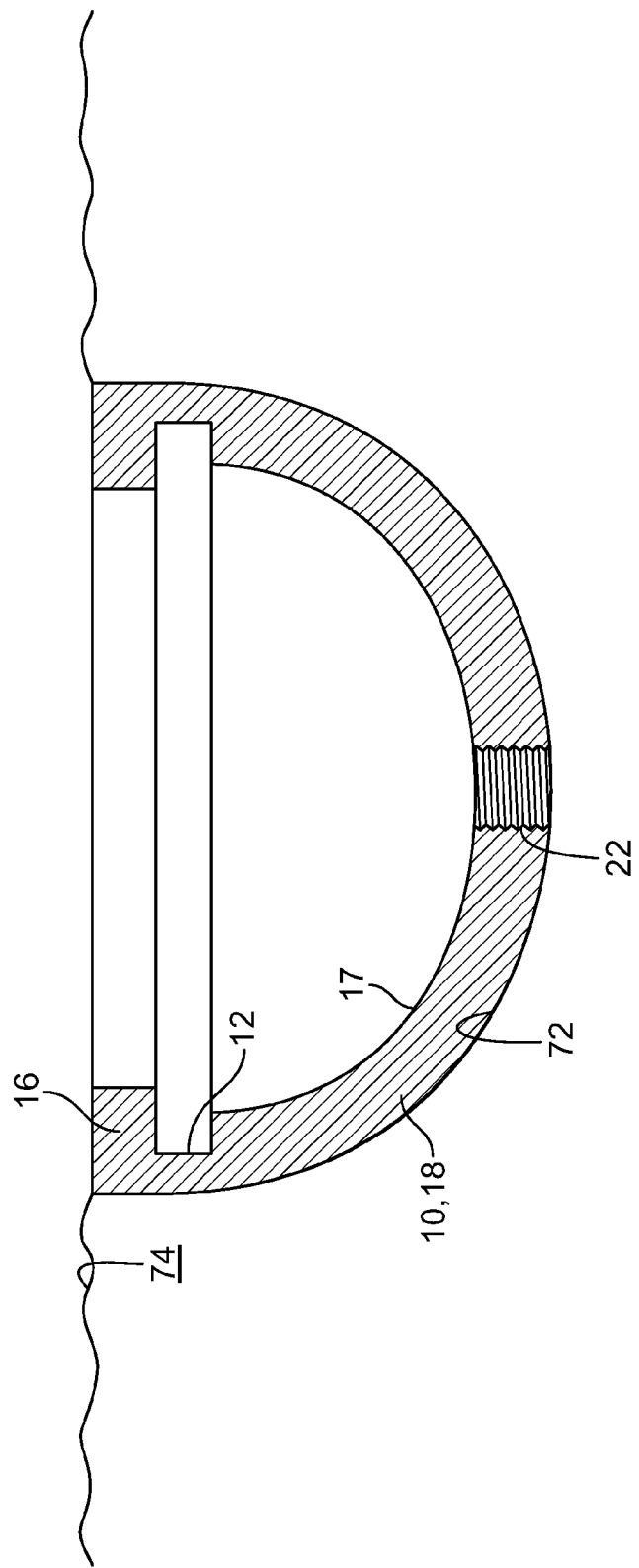

In some embodiments, the impaction force simultaneously snaps off the guide 30 from the implant 10. For example, as shown in FIG. 8B, an impact force, F, applied to the impactor 50 is translated via the aperture 22 to the implant body 18, which drives the edge 16, and thereby the implant 10 as a whole, downward in the direction of the applied impact force, F. Because the flange 40 is flexible, the flange 40 bends or otherwise displaces inwardly (e.g., away from the inner surface 17 of the implant 10) in the direction of arrow A and thereby releases the edge 16 of the implant 10 from the slot 44. In some embodiments, however, the surgeon manually snaps off the guide 30 from the implant 10 either before or after impaction. For example, to remove the impactor 50, the surgeon can unscrew the threaded connection at the aperture 22 and distal end 54 of impactor 50. Then the surgeon can slide the attachment 52 off the impactor 50 and slide the impactor 50 out of the guide 30 through central aperture 36 or through the opening 31. As shown in FIG. 8C, the guide 30 is removed from the implant 10 (e.g., from manual snapping or from the force of impaction) and the implant 10 is left within the acetabulum 72 in the desired orientation (e.g., along implant axis 130 of FIG. 7A).

Figure 9:
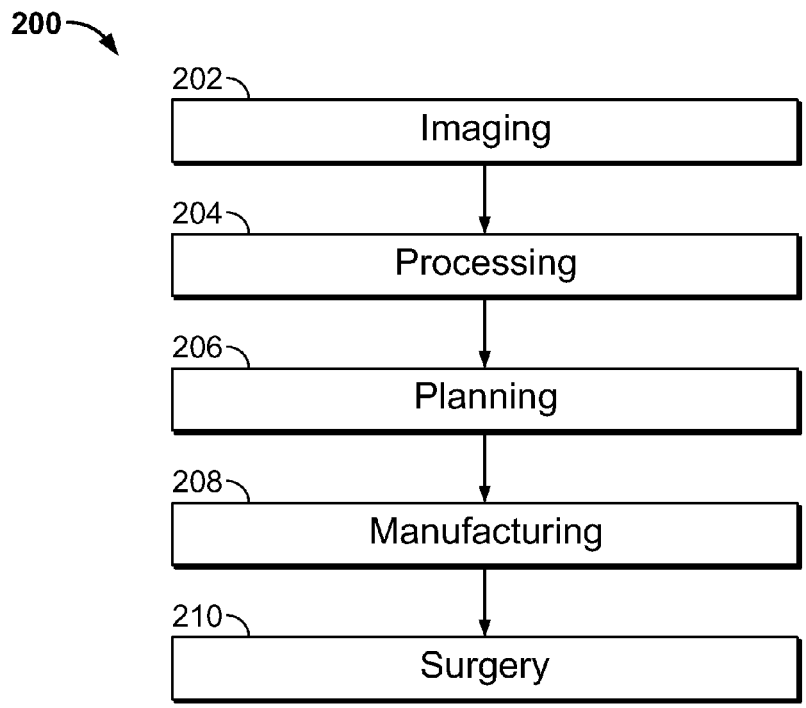
FIG. 9 shows an illustrative flow chart for planning and executing an orthopedic procedure using patient-matched components.

FIG. 9 shows an illustrative flow chart for preoperatively planning and executing an orthopedic procedure using patient-matched components according to certain embodiments. Preferably, the process defines abduction and anteversion angles for the placement of an implant, which, in turn, determines the orientation of the surgical preparation device. For example, the steps of FIG. 9 may be for a procedure on a patient's acetabulum 72. As schematically shown by FIG. 9, the process 200 includes the steps of imaging 202, processing 204, planning 206, manufacturing 208, and performing the surgery 210, although, in some embodiments, at least some of these steps are optional and other steps could be included. A wide variety of systems may be utilized in performing the process 200 shown in FIG. 9.

Figure 10:
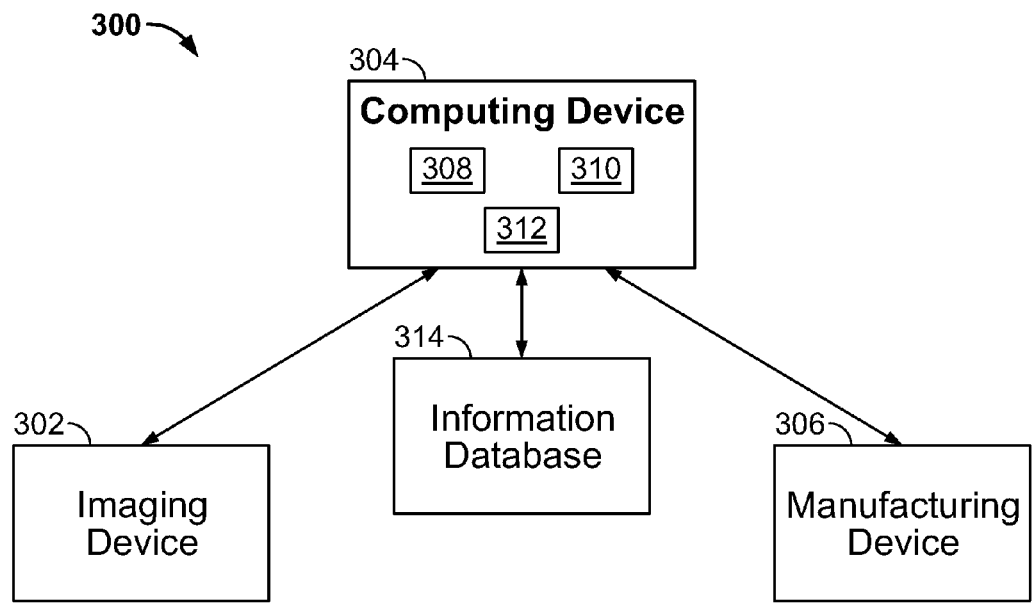
FIG. 10 schematically illustrates a system for facilitating the steps of the process depicted in FIG. 9.

For example, FIG. 10 schematically illustrates a system 300 for facilitating at least some steps of process 200. The system 300 includes an imaging device 302, computing device 304, and manufacturing device 306.

In some embodiments, certain steps of process 200, such as processing 204 and planning 206, may be carried out, wholly or at least partially, using a computing device 304. The computing device 304 may be part of or remote from imaging device or devices 302 used to image the patient and the manufacturing device or devices 306 used to custom manufacture instrumentation, implants or other devices for carrying out the procedure. Computing device 304 may receive or access data reflecting the images of the patient from imaging device 302 through any appropriate communication medium, including, but not limited to, wireline, wireless, optical, magnetic, solid state communication mediums, any other suitable communication medium, or any combination thereof. The computing device 304 represented in FIG. 10 includes a processor 308 that can execute code stored on a computer-readable medium, such as a memory 310. The computing device 304 may be any device that can process data and execute code that is a set of instructions to perform actions. Examples of the computing device 304 include a database server, a web server, desktop personal computer, a laptop personal computer, a server device, a handheld computing device, a mobile device, any other suitable device, or combinations thereof.

In some embodiments, the processor 308 may include a microprocessor, an application-specific integrated circuit (ASIC), a state machine, any other suitable processor, or combinations thereof. The processor 308 may include one processor or any number of processors and may access code stored in the memory 310. The memory 310 may be any non-transitory computer-readable medium capable of tangibly embodying code. The memory 310 may include electronic, magnetic, or optical devices capable of providing processor 308 with executable code. Examples of the memory 310 include random access memory (RAM), read-only memory (ROM), a floppy disk, compact disc, digital video device, magnetic disk, an ASIC, a configured processor, any other suitable storage device, or any combination thereof.

In some embodiments, the computing device 304 may share and/or receive data with additional components through an input/output (I/O) interface 312. The I/O interface 312 may include a USB port, an Ethernet port, a serial bus interface, a parallel bus interface, a wireless connection interface, any other suitable interface capable of allowing data transfers between the computing device and another component, or combinations thereof. The additional components may include components such as an information database 314. In some embodiments, the computing device 304 includes the information database 314.

The patient's anatomy of interest may be imaged using one or more non-invasive imaging technologies, including, but not limited to, computed tomography (CT), magnetic resonance imaging (MRI), X-ray, digital X-ray, ultrasound, any other suitable imaging technology, or any combination thereof. In embodiments using imaging technologies such as CT, MRI, or others, one or more sets of parallel image slices of the patient's anatomy may be obtained, including, for example, a series of transverse slices, sagittal slices, coronal slices, other angulations of slices, or combinations of series thereof. In some embodiments, multiple imaging technologies may be used for the same patient (e.g., X-ray for broader imaging of the overall patient, including other joints, and MRI for the joint of particular interest). The images of the patient's anatomy may, optionally, also include images of existing implants or portions thereof. In some embodiments, non-image based technologies may be used to obtain patient specific information about the patient's anatomy and geometries or other features associated therewith.

Image processing 204 is the next step in the process 200 of FIG. 9, in which at least some of the images may be processed to create an accurate three-dimensional ("3D") model, other multi-dimensional representation, or other virtual construct representing the geometries and/or selected features of the patient's particular anatomy. In some embodiments, such processing involves segmentation of the images (e.g., separation of at least one set of image slices) to distinguish the anatomy and other structures of interest from the surrounding anatomy and other structures appearing in the image. For example, in certain embodiments, portions of the acetabular rim, including bony or other tissue surfaces associated with the acetabular rim, may be segmented and distinguished from other portions of the images.

In some embodiments, segmentation may be accomplished by manual, automated, or semi-automated processes or any combination thereof. For example, in some embodiments, a technician or other user may (with the assistance of computer assisted design hardware and/or software or other functionality) manually trace the boundary of the anatomy and other structures of interest in each image slice. Alternatively, or additionally, in some embodiments, algorithms or other automated or semi-automated processes could be used to automatically identify the boundaries of interest. In some embodiments, only key points on the anatomy or other structures of interest may be segmented. Processing steps 204 as described above may be used to make a 3D model of the patient's anatomy and other features of interest.

The 3D model or other construct representing the patient's anatomy may be used for pre-surgical planning 206 of the surgical procedure. In some embodiments, pre-surgical planning 206 can include one or more of identifying a desired position and orientation of a implant 10 within the acetabulum, and/or designing a guide 30 comprising a patient-matched surface 38 to conform to portions of an acetabular rim. In various embodiments, the planning 206 may be carried out using manual, semi-automated, or automated functionality.

As described above, the guide 30 may include one or more surfaces 38 that are specifically designed to mimic the patient's particular anatomy (or portions thereof) as determined, for example, by the 3D model of the anatomy. For example, in some embodiments, the patient-matched surface or surfaces 38 can be a negative mold of the patient's anatomy such that the surface 38 uniquely conforms to the patient's anatomy in one particular position and orientation. In other words, the patient-matched surface or surfaces 38 may facilitate achieving a desired position and/or orientation of the guide 30 with respect to the patient's particular anatomy because the patient-matched surface 38 will allow the guide 30 to fully seat on the patient's particular anatomy only when the guide 30 is in the desired position and/or orientation. The guide 30 may be formed using the patient-matched data to include an opening 31 in the guide body 32, where the patient-matched surface or surfaces 38 are provided about the opening 31 on the bottom surface 37 of the guide 30. In some embodiments, a crossbar 34 is provided that extends across the opening 31. The crossbar 34 may be integrally formed with the opening 31 or may be removably placeable within the opening 31.

In some embodiments, the geometries and other aspects of the patient-matched surface 38 are determined in the planning stage 206 by applying a blank (e.g., a wire-frame or similar digital representation) to the 3D model of the patient's anatomy such that the guide 30 is in the desired position and orientation with respect to the patient's anatomy, and then removing from or adding to portions of the blank to create the patient-matched surface 38 conforming to the surface of the patient's anatomy. In some embodiments, other processes performed during the planning stage 206 determine, at least partially or wholly, the position and/or orientation of the blank relative to the 3D model of the patient's anatomy. For example, during planning 206 the position and orientation of the implant 10 may be defined with respect to the patient's acetabulum 72. The planned position of the implant 10 may be used, in combination with the 3D model of the patient's anatomy or the blank, to define the particular shape and other attributes of the guide 30.

Once designed, the guide 30 may be manufactured (step 208 in process 200) using any number of known technologies, including, but not limited to, selective laser sintering, 3D printing, stereo-lithography, other rapid production or custom manufacturing technologies, or any combination thereof. In some embodiments, the manufacturing devices 306 can be remote from the computing devices 304 involved in the processing 204 and planning 206, and data or other information sufficient to manufacture the patient-matched instruments can be exported from the computing devices 304 to the manufacturing devices 306 in any desirable format.

The foregoing is merely illustrative of the principles of the disclosure, and the systems, devices, and methods can be practiced by other than the described embodiments, which are presented for purposes of illustration and not of limitation. It is to be understood that the systems, devices, and methods disclosed herein, while shown for use in acetabular systems, may be applied to systems, devices, and methods to be used in other surgical procedures including, but not limited to, spine arthroplasty, cranio-maxillofacial surgical procedures, knee arthroplasty, shoulder arthroplasty, as well as foot, ankle, hand, and extremities procedures.

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

What is claimed is:

1. A method for aligning an orthopedic implant, the orthopedic implant having an undercut disposed on an inner surface, the method comprising:
    coupling a guide to the inner surface of the orthopedic implant using a snap-fit flange to engage the undercut, wherein the guide has a guide body and a patient-matched surface with a predetermined configuration that corresponds to a respective anatomic landmark site;
    aligning the orthopedic implant using the patient-matched surface of the guide by placing the guide in the predetermined configuration by matching the guide with the respective anatomic landmark site;
    removing the guide from the orthopedic implant by actuating the snap-fit flange;
    coupling the guide to an impactor; and
    applying a force using the impactor, wherein the force simultaneously sets the implant in a preferred orientation and actuates the snap-fit flange to decouple the guide from the implant.

2. The method of claim 1, further comprising determining the fit of the orthopedic implant by viewing the orthopedic implant through an opening in the guide.

3. The method of claim 1, further comprising coupling the orthopedic implant to the impactor.

4. The method of claim 3, further comprising placing an attachment piece onto the impactor at a position between the guide and the orthopedic implant.

5. The method of claim 1, wherein the implant is free to rotate when the guide makes contact with a patient's anatomy.

6. A method for aligning an orthopedic implant, the orthopedic implant having an undercut disposed on an inner surface, the method comprising:
    coupling a guide to the inner surface of the orthopedic implant using a snap-fit flange to engage the undercut, wherein the guide has a guide body and a patient-matched surface with a predetermined configuration that corresponds to a respective anatomic landmark site;
    aligning the orthopedic implant using the patient-matched surface of the guide by placing the guide in the predetermined configuration by matching the guide with the respective anatomic landmark site;
    mounting the guide to a shaft of an impactor;
    coupling the orthopedic implant to the shaft of the impactor; and
    applying a force using the impactor such that the force simultaneously sets the implant in a preferred orientation and actuates the snap-fit flange to decouple the guide from the implant.

7. The method of claim 6, further comprising placing an attachment piece onto the impactor at a position between the guide and the orthopedic implant.

8. A method for aligning an orthopedic implant, the orthopedic implant having an undercut disposed on an inner surface, the method comprising:
    coupling a guide to the inner surface of the orthopedic implant using a snap-fit flange to engage the undercut, wherein the guide has a guide body and a patient-matched surface with a predetermined configuration that corresponds to a respective anatomic landmark site;
    aligning the orthopedic implant using the patient-matched surface of the guide by placing the guide in the predetermined configuration by matching the guide with the respective anatomic landmark site;
    coupling the implant to an impactor; and
    applying a force using the impactor and removing the guide from the orthopedic implant by actuating the snap-fit flange, wherein the force simultaneously sets the implant in a preferred orientation and actuates the snap-fit flange to decouple the guide from the implant.

* * * * *